(12) United States Patent
Erickson et al.

(10) Patent No.: US 6,416,547 B1
(45) Date of Patent: Jul. 9, 2002

(54) HEART VALVE CARRIER AND RINSE CAGE

(75) Inventors: Stephen M. Erickson, Irvine; Leslie Pathmanaban, Lake Forest; Michael J. Numamoto, Irvine; Than Nguyen, Fullerton, all of CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 107 days.

(21) Appl. No.: 09/665,872

(22) Filed: Sep. 20, 2000

(Under 37 CFR 1.47)

Related U.S. Application Data

(63) Continuation of application No. 09/413,571, filed on Oct. 6, 1999, now abandoned.

(51) Int. Cl.$^7$ .................................................. A61F 2/24
(52) U.S. Cl. ...................................... 623/2.11; 206/438
(58) Field of Search ................................ 623/2.1, 2.11, 623/FOR 101, 2.12–2.19, 2.42; 206/438

(56) References Cited

U.S. PATENT DOCUMENTS

| | | | |
|---|---|---|---|
| 2,565,899 A | 8/1951 | Wilcox |
| 2,716,504 A | 8/1955 | Martin |
| 2,721,567 A | 10/1955 | Tierney |
| 2,744,647 A | 5/1956 | Wheaton et al. |
| 3,612,326 A | 10/1971 | Marks |
| 3,792,794 A | 2/1974 | Cutter et al. |
| 3,871,543 A | 3/1975 | Chadfield et al. |
| 4,065,816 A | 1/1978 | Sawyer |

(List continued on next page.)

FOREIGN PATENT DOCUMENTS

| | | |
|---|---|---|
| WO | WO95/17139 | 6/1995 |
| WO | WO0040176 | 7/2000 |

*Primary Examiner*—David H. Willse
(74) *Attorney, Agent, or Firm*—Debra D. Condino; John Christopher James; Guy L. Cumberbatch (57) ABSTRACT

A carrier for heart valves allows the removal of a heart valve from the carrier without manual manipulation. In addition, the carrier minimizes or substantially eliminates leaking of preserving fluid during transportation and storage. The carrier includes a jar, a rinse cage, and a holder to which a heart valve is attachable. The rinse cage includes a first engagement structure, for example, a channel, and the holder includes a second engagement structure, for example, a groove, complementary to the first engagement structure for releasably engaging therewith. A heart valve attached to the holder is disposed or suspended within the rinse cage when the engagement structures are engaged. A heart valve attached to the holder is protected not only when within the jar but also when removed from the jar. The holder has a socket for engaging with a surgical handle used to remove the valve from the jar for rinsing and implantation. The carrier may include apparatus for limiting rotation of the holder relative to the rinse cage and rotation of the rinse cage relative to the jar, which apparatus allows a surgical handle to be securely and firmly attached to the holder with essentially one hand and without removing the valve from the jar. The jar includes a lid that may have a rotatable gasket and a flange. The jar may have an apex-like top surface for making a compressive seal against the gasket when the lid is tightened. The flange may have a vent for allowing gases between the gasket and the lid to escape during sterilization processes of the carrier.

29 Claims, 6 Drawing Sheets

U.S. PATENT DOCUMENTS

| | | |
|---|---|---|
| 4,101,031 A | 7/1978 | Cromie |
| 4,106,655 A | 8/1978 | Heijting |
| 4,109,815 A | 8/1978 | Collins, III |
| 4,182,446 A | 1/1980 | Penny |
| 4,200,196 A | 4/1980 | Bashour |
| 4,211,325 A | 7/1980 | Wright |
| 4,377,175 A | 3/1983 | Fritz |
| 4,512,471 A | 4/1985 | Kaster et al. |
| 4,597,658 A | 7/1986 | Buelens et al. |
| 4,801,015 A | 1/1989 | Lubock et al. |
| 4,881,562 A | 11/1989 | Wright et al. |
| 5,184,544 A | 2/1993 | Ling |
| 5,560,487 A | 10/1996 | Starr |
| 5,720,391 A | 2/1998 | Dohm et al. |
| 5,800,531 A | 9/1998 | Cosgrove et al. |

HEART VALVE CARRIER AND RINSE CAGE

This is a continuation, Divisional, Continuation-in-part, application 09/413,571, filed Oct. 6, 1999, now abandoned.

BACKGROUND OF THE INVENTION

1. Field of the Invention

The present invention relates to carriers for holding heart valves during storage and transportation and, more particularly, to carriers for holding heart valves made from natural tissue (known as bioprosthetic heart valves).

2. Description of the Related Art

To minimize the possibility of damage to a relatively delicate medical device, bioprosthetic heart valves are packaged in jars filled with preserving solution for shipping and storage prior to use in the operating theater. In doing so, the valves are stabilized to prevent the valves from striking the inside of the jar.

Prior to implantation in a patient, residual traces of the preserving solution need to be washed from the valve. This washing is accomplished by first removing the valve from the jar and then rinsing the valve in a shower. Alternatively, the valve may be immersed and agitated in a bath. First, the medical personnel removes the valve from its jar by grasping a valve holder with a gloved hand. The valve holder is typically centrally located with respect to, and sutured to, the valve sewing ring. A surgical handle is then threaded into a socket provided in the valve holder. The valve is then rinsed in the bath or shower while being held at the end of the handle. After rinsing, the handle is used to position the valve in the appropriate implantation site. This conventional process leaves the valve susceptible to damage if the valve strikes a surface while being manipulated on the end of the surgical handle.

In addition to the susceptibility for damage to the valves in the operating theater, the transportation of the valves to the operating theater also introduces problems. Heart valves are often shipped to customers, that is, hospitals, via aircraft. The valves, packed in jars as described above, are stored in the cargo hold of the aircraft during flight, which is a low-pressure and low-temperature environment. With conventional packaging approaches, there has been the possibility of leakage of the preserving fluid during transport in such environments, which is undesirable. With leakage, the integrity of the sterilization of the valve is suspect.

In view of the foregoing, it is apparent that there is still a need in the art for a carrier for heart valves that enables a medical practitioner to easily and safely remove and rinse a valve, as well as attached a surgical handle thereto. In addition, there is also a need in the art for a carrier for heart valves that does not leak during transportation, even in low-pressure environments.

SUMMARY OF THE INVENTION

The present invention provides a carrier for heart valves that overcomes the disadvantages of conventional approaches to the packaging of heart valves. The carrier of the present invention enables a medical practitioner to first connect the surgical handle to the valve holder while the heart valve remains in its shipping carrier. In addition, the carrier of the present invention is configured to minimize or substantially eliminate leaking of preserving fluid during transportation and storage.

According to one aspect of the invention, a carrier for a heart valve includes a jar, a rinse cage receivable within the jar, and a holder to which a heart valve is attachable, for example, by sewing apparatus. The rinse cage includes a first engagement structure, and the holder includes a second engagement structure complementary to the first engagement structure for releasably engaging therewith. The engagement structures are configured such that when engaged, a heart valve attached to the holder is disposed within the rinse cage.

One of the advantages of the carrier of the present invention is that a heart valve attached to the holder is protected not only when within the jar but also when removed from the jar. More specifically, when the holder is removed from the jar, the rinse cage with the valve suspended therein is also removed because the two components are engaged. Accordingly, the heart valve may be rinsed outside of the jar while still being received within and protected by the rinse cage.

To facilitate the removal of the holder-and-rinse cage combination, the holder preferably has a socket for engaging with a surgical handle. A medical practitioner may attach a surgical handle to the holder to remove the valve from the jar while the valve is still received within the rinse cage in the jar. Accordingly, the practitioner does not need to manually remove and hold the valve to attach a handle.

To facilitate the engagement of the surgical handle, the carrier may include a stop which is configured to limit rotation of the holder relative to the rinse cage, and locking apparatus which is configured to limit rotation of the rinse cage relative to the jar. Accordingly, as a surgical handle is tightened into the socket, frictional forces cause the holder to rotate. However, the stop limits the rotation by engaging with the rinse cage. As the handle is further tightened, frictional forces cause the rinse cage to rotate, which rotation is limited by the locking apparatus. Accordingly, a medical practitioner is able to engage a surgical handle securely and firmly without needing to manually remove the valve from the jar.

According to another aspect of the invention, the carrier includes a lid attachable to the jar. A lid has a gasket that is held rotatable relative to the lid with a flange. To form a seal with integrity, a top surface of the jar is tapered to define an apex. When the lid is attached to the jar, the apex contacts and compresses the gasket as the lid is tightened, without the gasket rotating responsively with the lid. To further increase the integrity of the seal, the flange may include a vent for allowing gases between the gasket and the lid to escape during sterilization processes of the carrier.

Other aspects, features, and advantages of the present invention will become apparent to those skilled in the art from a consideration of the following detailed description taken in conjunction with the accompanying drawings which illustrate, by way of example, the principles of the present invention in the context of a carrier for heart valves, but which are equally relevant to other carriers in which items are stored or transported.

DETAILED DESCRIPTION OF THE INVENTION

Figure 1:
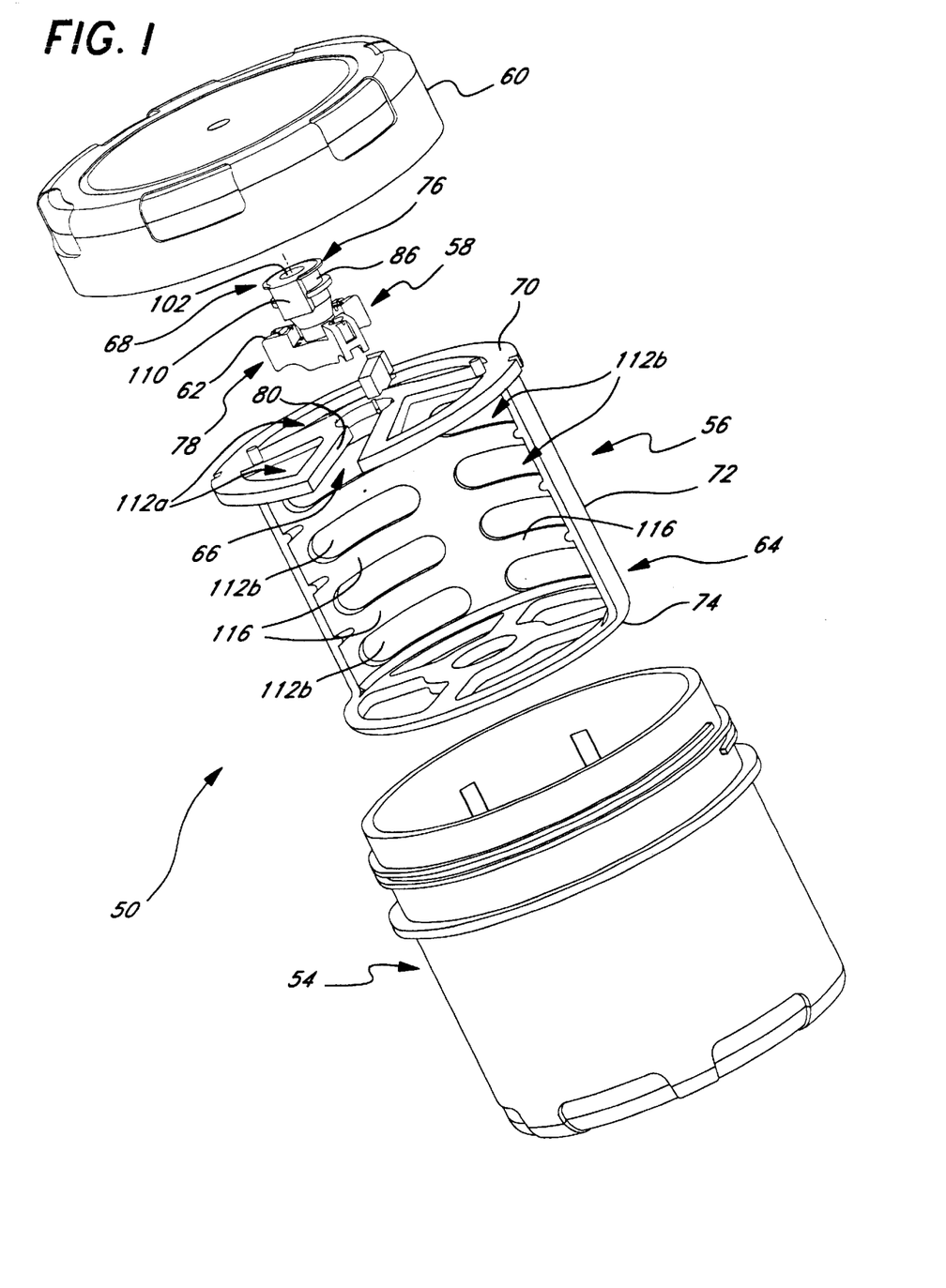
FIG. 1 is an exploded perspective view of an exemplary carrier for holding a heart valve in accordance with the present invention.
Figure 2:
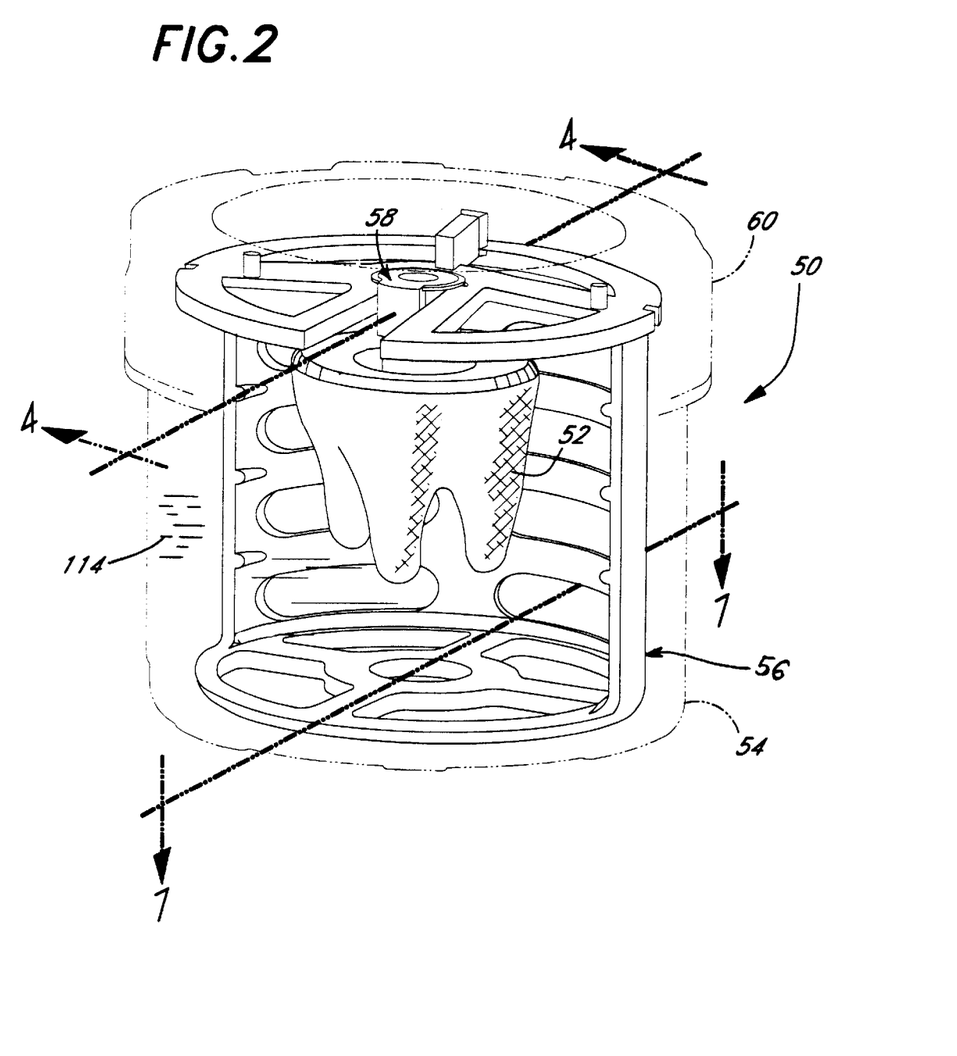
FIG. 2 is a perspective view of the carrier of the invention, particularly illustrating the carrier holding a heart valve.

Referring more particularly to the drawings, a carrier 50 for holding a bioprosthetic heart valve 52 is shown in FIGS. 1 and 2 in an exemplary embodiment according to the present invention. Exemplary carrier 50 generally includes a jar 54, a rinse cage 56, and a holder 58. The jar 54 is sealable with a lid 60. The rinse cage 56 is receivable within the jar 54, as shown in FIG. 2. The holder 58 is releasably engageable with the rinse cage 56 and has sewing apparatus 62 to which a valve is releasably attachable. Desirably, the sewing apparatus 62 comprises eye-holes and/or notches to which the sutures may be fastened.

Exemplary carrier 50 of the present invention enables a medical practitioner to remove the heart valve 52 from the jar 54 without having to manually grasp the valve 52, the rinse cage 56, the holder 58, or any other element of the carrier except the jar. In addition, exemplary carrier 50 is configured to ensure a leak-proof seal between the jar 54 and the lid 60, even while in low-pressure environments such as cargo holds in airplanes. These and additional features of the present invention are discussed in detail below.

Exemplary rinse cage 56 includes a frame 64 with first engagement structure 66 disposed thereon. In addition to the sewing apparatus 62, exemplary holder 58 includes second engagement structure 68 complementary to the first engagement structure 66 of the rinse cage 56 so that the engagement structures may be releasably coupled. More particularly and as shown in FIG. 2, when the engagement structures 66 and 68 are engaged, the heart valve 52 attached to the sewing apparatus 62 of the holder 58 is disposed within the rinse cage 56.

Figures 3, 5, 6:
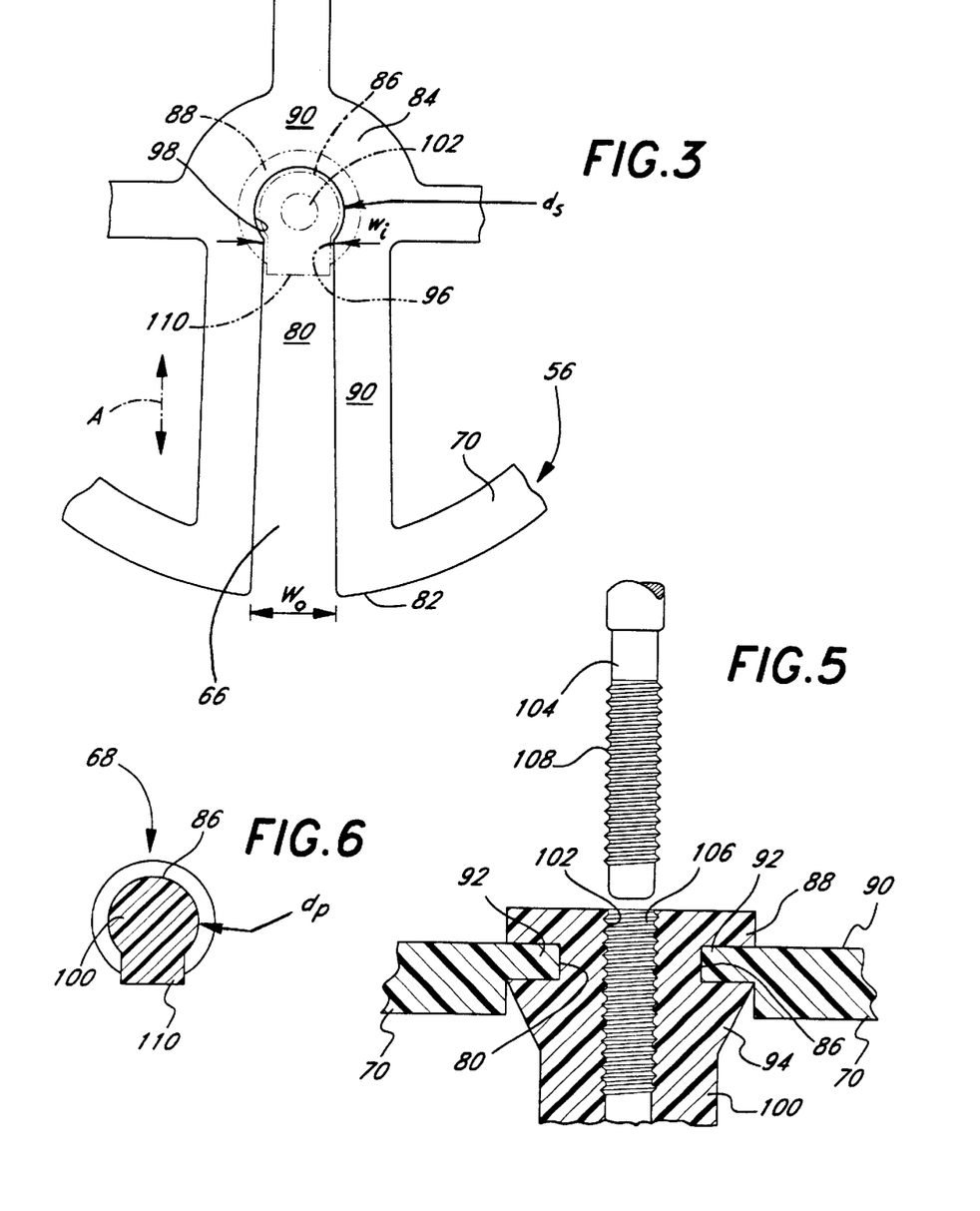
FIG. 3 is a plan view of a portion of a rinse cage of the carrier, particularly illustrating a holder (shown in phantom line) engaged with the rinse cage.
FIG. 5 is a cross-sectional view of exemplary engagement apparatus of the invention for engaging the holder with the rinse cage.
FIG. 6 is a cross-sectional view of exemplary rotation-limiting apparatus of the invention for limiting the rotation of the holder when engaged with the rinse cage.
Figure 4:
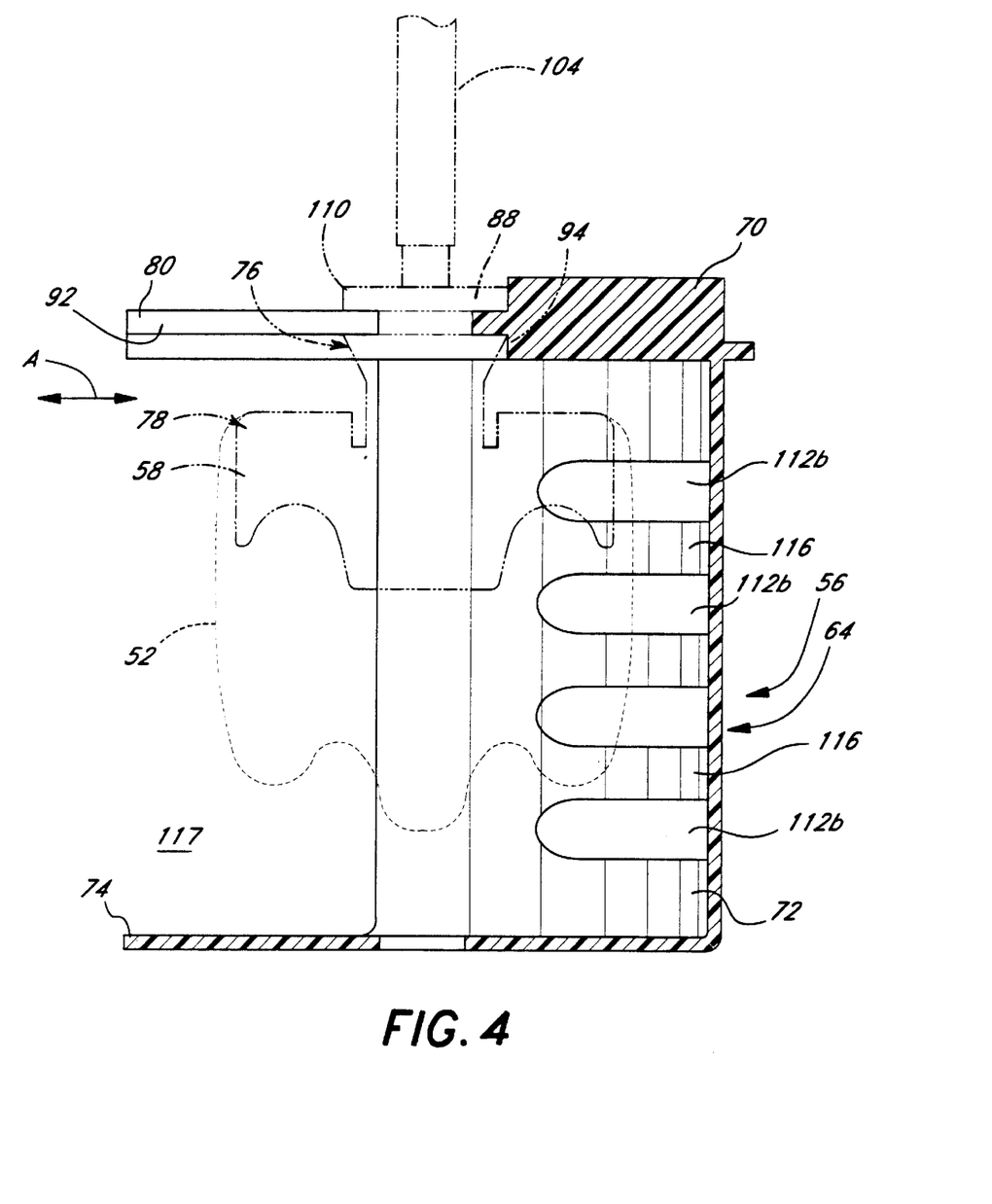
FIG. 4 is a vertical cross-sectional view of the rinse cage of the invention taken along line 4—4 of FIG. 2, particularly illustrating a holder with a heart valve attached thereto (shown in phantom line) engaged with the rinse cage.

With reference to FIGS. 3 and 4, an exemplary embodiment of the engagement structures 66 and 68 is shown in which the second engagement structure 68 of the holder 58 engages with the first engagement structure 66 of the rinse cage 56 in a sliding motion. More particularly, and with reference also to FIG. 1, exemplary rinse cage 56 has a planar, circular, top member 70, a tubular side member 72, and a planar, circular bottom member 74, and exemplary holder 58 has a top portion 76 and a bottom portion 78. Desirably, and as described below, top member 70, side member 72, and bottom member 74 are all perforated to permit fluid flow therethrough. First engagement structure 66 is disposed on the top member 70 of the rinse cage 56 and may include a channel 80 formed therein, extending from an outer edge 82 thereof to an inner portion 84 thereof. Exemplary second engagement structure 68 is disposed on the top portion 76 of the holder 58 and may include a groove 86 between top and bottom portions 76, 78 which is slidable within the channel 80.

With additional reference to FIG. 5, when the groove 86 is disposed within the channel 80, an upper lip 88 of exemplary second engagement structure 68 rests upon a top surface 90 of the top member 70 of the rinse cage 56, thereby suspending the bottom portion 78 below the top member 70 and within the rinse cage 56, as particularly shown in FIG. 4. To engage, the groove 86 is positioned at the outer edge 82 of the channel 80, and the holder 58 is slid inward; to disengage, the holder 58 is slid outward, which sliding motion is shown by arrows A in FIGS. 3 and 4.

As particularly shown in FIG. 5, the channel 80 of exemplary first engagement structure 66 may be configured to form a pair of opposing rails 92 in a spaced relationship across the channel 80. Further, exemplary second engagement structure 68 may also have a lower lip 94 disposed in a spaced relationship with the upper lip 88 across the groove 86, so that the groove 86 acts as a race in which the rails 92 are slidably receivable. In this particularly exemplary embodiment, the groove 86 has a thickness that is greater than or equal to a thickness of the rails 92, preferably slightly greater than, to provide a secure engagement therebetween.

With particular reference to FIG. 3, the channel 80 of exemplary first engagement structure 66 has a width w that preferably decreases from the outer edge 82 (i.e., width $w_o$) to the inner portion 84 (i.e., width $w_i$). Accordingly, exemplary channel 80 has a neck 96 defined at the inner portion 84 thereof. In addition, exemplary channel 80 may have a seat 98 formed at the inner portion 84 thereof. With reference to FIG. 6, exemplary second engagement structure 68 of the holder 58 has a central post 100 around which the groove 86 is formed. The seat 98 has a diameter $d_s$ (FIG. 3), and the post 100 has a diameter $d_p$ (FIG. 6).

According to the exemplary embodiment of the invention shown in the drawings, diameter $d_s$ of the seat 98 is greater than to diameter $d_p$ of the post 100, and diameter $d_p$ of the post 100 is greater than or equal to width $w_i$ of the neck 96 such that the post 100 is urgeable through the neck 96, thereby "snapping" into the seat 98. When the post 100 is received within the seat 98, the upper lip 88 is positioned upon the portion of the top surface 90 surrounding the seat 98, thereby suspending the bottom portion 78 of the holder 58, as well as a heart valve attached to the sewing apparatus 62, between the top member 70 and the bottom member 74 of the rinse cage 56. To disengage, the post 100 is urged outward through the neck 96, thereby snapping out of the seat 98. The suspension of the heart valve 52 within the confines of the rinse cage 56 prevents the valve from contacting any surface (i.e., the frame 64 and the jar 54) during shipping and handling, thereby preventing any damage to the valve.

With reference to FIGS. 1 and 3–5, exemplary holder 58 may include a socket 102 disposed in the top portion 76 thereof for engaging with a surgical handle 104. The socket 102 is disposed on the holder 58 such that the socket 102 is above the frame 64 when the engagement structures 66 and 68 are engaged, as particularly shown in FIG. 4. For example, the socket 102 may extend downward through the post 100, as shown in FIGS. 4 and 5. The socket 102 may have inner threading 106 for engaging with complementary threading 108 on the surgical handle 104. When the engagement structures 66 and 68 are engaged, for example, when the post 100 is received in the seat 98, the surgical handle 104 may be engaged with the socket 102 to maneuver the holder 58 in and out of the rinse cage 56.

When engaging with the holder 58, the handle 104 is rotated into the socket 102. Because of frictional forces on the respective threading 106 and 108 of each of these elements, the holder 58 may rotate responsively, particularly as the engagement begins to tighten. To facilitate a secure engagement of the handle 104 with the socket 102, rotation-limiting apparatus may be provided to limit rotation of at least the socket 102, if not the holder 58 as a whole, allowing the handle 104 to be forcibly rotated into the socket 102. The rotation-limiting apparatus may include a stop 110 that is configured to limit rotation of the post 100 and, accordingly, the socket 102 and the holder 58 when the post 100 is received in the seat 98. More specifically, as seen in FIG. 6, exemplary stop 110 projects outward from the post 100 such that when the post 100 is received within the seat 98, the stop 110 projects through the neck 96 and into the channel 80, as particularly shown in FIG. 3 in phantom line. Exemplary stop 110 may have a width that is less than or equal to width $w_i$ at neck 96 so that the neck 94 limits rotation of the stop 110 and, accordingly, the holder 58. Additional advantages of the rotation-limiting apparatus will be discussed in detail below.

With reference to FIGS. 1 and 2, at least one of the members (i.e., the top member 70, the side member 72, and/or the bottom member 74) of the frame 64 of the rinse cage 56 has at least one opening 112 formed therein. The openings 112 formed in the top member 70 of the frame 64 are specifically indicated by reference numeral 112a; the openings 112 formed in the side member 72, by reference numeral 112b; and the openings in the bottom member 74, by reference numeral 112c. The openings 112 in the frame 64 allow fluid 114 contained in the jar 54 for preserving the valve 52 to flow freely through the rinse cage 56. In addition, the openings 112 in the frame 64 allow the valve 52 to be rinsed in a shower or immersed in a bath to remove residual traces of the fluid 114 when the rinse cage 56 and the holder 58 are removed from the jar 54 with the surgical handle 104. After the valve 52 has been rinsed, the holder 58 may be disengaged from the rinse cage 56 and positioned at a surgical site.

Referencing FIGS. 1 and 4, openings 112b formed in the side member 72 of the frame 64 may be formed as a plurality of substantially circumferential openings so that a plurality of circumferential ribs 116 are defined. The ribs 116 provide not only support to the frame 64 but also protection to the valve 52 attached to the holder 58 when received within the jar 54 and when the engagement structures 66 and 68 are engaged. More specifically, when the engaged rinse cage-and-holder combination is removed from the jar 54 with the surgical handle 104, the valve 52 attached to the holder 56 is protected not only from the top and bottom from the respective members 70 and 74 of the frame 64 but also about a substantial extent laterally from the side member 72, as particularly shown in FIG. 4. For example, exemplary rinse cage 56 may be configured so that the side member 72 extends through an approximately 180-degree arc. Accordingly, the rinse cage-and-holder combination may be moved about, for example, during rinsing, prior to removing the holder-and-valve combination from the rinse cage 56, with a substantial degree of protection for the valve 52. The semi-cylindrical configuration of the frame 64 of the rinse cage 56 provides a correspondingly semi-cylindrical opening 116 through which the valve 52 passes when the holder 56 is engaged and disengaged with the rinse cage 56. In this respect, the channel 80 extends from inner portion 84 of top member 70 towards open side of side member 72.

Figure 7:
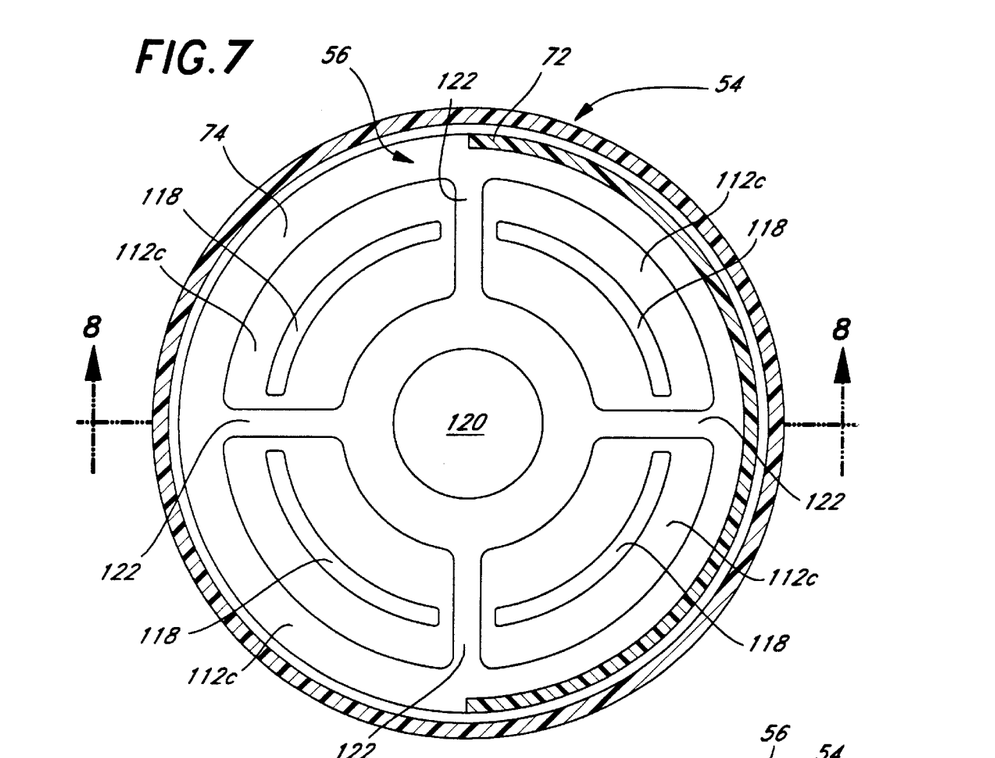
FIG. 7 is a horizontal cross-sectional view of the rinse cage received within a jar of the carrier taken along line 7—7 of FIG. 2, particularly illustrating locking apparatus for limiting the rotation of the rinse cage within the jar.
Figure 8:
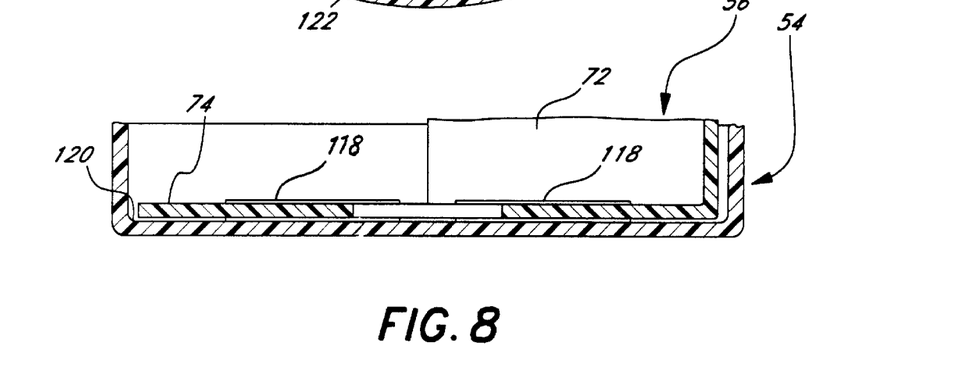
FIG. 8 is a cross-sectional view of the rinse cage received within the jar, particularly the locking apparatus, taken along line 8—8 of FIG. 7.

With additional reference to FIGS. 7 and 8, exemplary carrier 50 of the present invention may also include locking structure for limiting the rotation of the rinse cage 56 within the jar 54. Generally, the locking structure of the present invention may include a receptacle disposed on the rinse cage 56 and a protrusion 118 disposed on the jar 54, with the protrusion 118 being receivable within the receptacle. According to an exemplary embodiment of the invention, each of the openings 112c formed in the bottom member 74 of the frame 64 may serve as a receptacle for receiving a respective protrusion 118 of a plurality of protrusions disposed on a bottom 120 of the jar 54. The openings 112c define a plurality of spokes 122 therebetween. When engaged, the protrusions 118 respectively project upward into the openings 112c and are able to contact a respective spoke 122 to prevent rotation of the rinse cage 56 relative to the jar 54. As particularly shown in FIG. 7, the protrusions 118 may be configured to complement the shape of the openings 112c; for example, in the exemplary embodiment shown, the protrusions 118 and the openings 112c are substantially arcuate.

One of the advantages of the rotation-limiting apparatus (i.e., the stop 110) and the locking apparatus (i.e., the protrusions 118 and the openings 112c), as well as the engagement structures 66 and 68, of the present invention is that a medical practitioner may not only engage the surgical handle 104 with the socket 102 in a secure manner but may also remove the combination of the heart valve 52, the holder 58, and the rinse cage 56 in a quick and easy manner. More specifically, to remove the heart valve 52 from the jar 54, the surgical handle 104 is engaged with the socket 102 by rotating. When the frictional forces of the threading 106 and 108 cause the holder 58 to rotating, the stop 110 engages the channel 80 to prevent further rotation of the holder 58. As the engagement of the handle 104 with the socket 102 becomes more secure, the frictional forces of the threading 106 and 108 cause the rinse cage 56 to rotate. However, rotation of the rinse cage 56 is limited or prevented by the protrusions 118 engaging with the spokes 122. Accordingly, holding the jar 54 in one hand and the surgical handle 104 in the other, a medical practitioner may firmly engage the surgical handle 104 with the holder 58 without putting pressure on, or otherwise handling, the heart valve.

Figure 9:
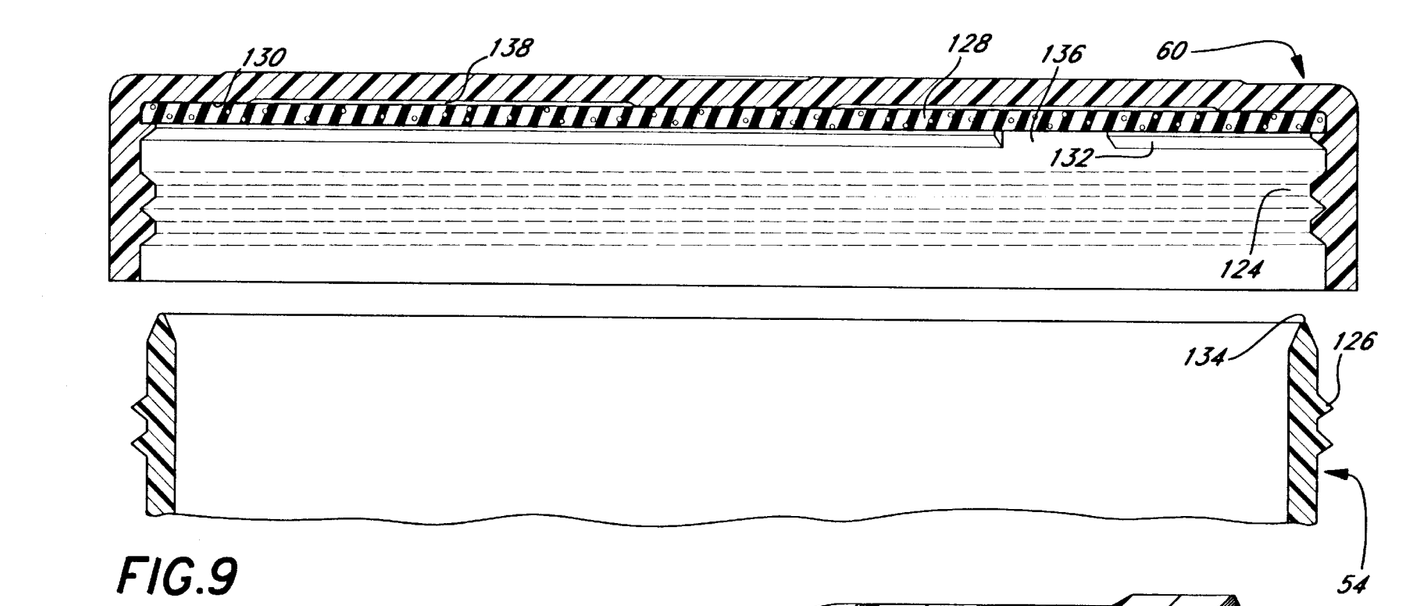
FIG. 9 is a cross-sectional view of the jar and a lid of the carrier of the present invention.

Referencing FIG. 9, the jar 54 and the lid 60 are shown in more detail. The lid 60 has threading 124 for engaging with complementary threading 126 of the jar 54. In addition, exemplary lid 60 includes a gasket 128 disposed against an inner top surface 130 thereof and retained by a flange 132. According to the present invention, exemplary gasket 128 is not fixed to the lid 60 but is rather able to move or rotate independently of the lid 60. The rotatable gasket 128 facilitates the formation of a leak-proof seal between the lid 60 and the jar 54. To further facilitate the formation of a leak-proof seal, exemplary jar 54 may include a pointed top surface or apex 134.

Figure 10:
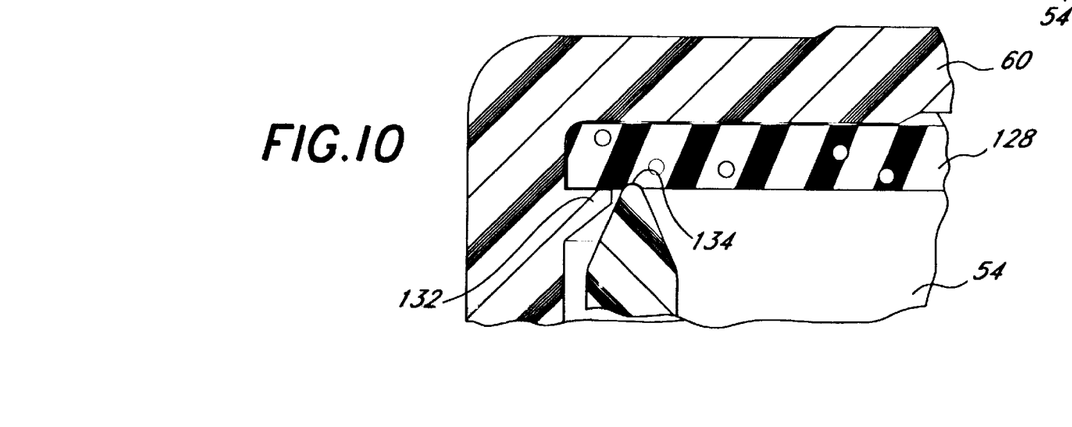
FIG. 10 is an enlarged cross-sectional view of the lid attached to the jar, particularly illustrating a seal formed therebetween.

More specifically, with reference to FIG. 10, when engaging the lid 60 with the jar 54, the apex 134 of the jar 54 comes into contact with the gasket 128. With continued tightening of the lid 60, the apex 134 compresses the gasket 128 and concentrates the sealing force at a relatively small contact area, thereby forming a substantially leak-proof the seal between the gasket 128 and the apex 134. The apex 134 is preferably rounded to reduce the possibility of damage to the gasket 128.

Referencing FIG. 9, exemplary lid 60 may include a vent 136 formed in the flange 132. Prior to receiving a heart valve, the carrier 50 is sterilized. The vent 136 allows gases between the gasket 128 and the inner surface 130 of the lid 60, for example, in an air space 138, to escape during sterilization processes. The efficient removal of gases between the gasket 128 and the lid 60 further improves the seal between the jar 54 (i.e., the apex 134) and the gasket 128, particularly when the carrier 50 is being transported in a low-pressure and low-temperature environment, for example, a cargo hold of an airplane. As gas disposed between the gasket 128 and the lid 60 is able to vent during the sterilization process, the seal made between the jar 54 and the gasket 128 is made at low pressure and, accordingly, will not be adversely affected when the carrier 50 is transported at in a low-pressure environment and then stored in an environment with relatively high pressure and temperature.

A further significant advantage of the present heart valve carrier is the ability to unify the handling process for a number of different heart valves. That is, the present carrier is capable of receiving a number of different types of heart valves, as long as the engagement structure on the valve holder matches the engagement structure on the rinse cage. So, for example, a number of heart valves can be mounted on the holder shown and described, which attaches via sutures to the cloth sewing ring. Other valves may be attached to a different holder that includes the second engagement structure 68 shown best in FIG. 1. With such flexibility, the steps of handling, shipping, receiving, handle attaching and rinsing are identical with all the heart valves.

Those skilled in the art will understand that the present invention is not limited to the specifically illustrated and described embodiments above. The scope of the present invention is determined by the terms of the appended claims and their legal equivalents, rather than by the examples described above.

What is claimed is:

1. A carrier for a heart valve, the carrier comprising:
   a rinse cage including a first engagement structure; and
   a holder to which a heart valve is attachable, the holder including a second engagement structure complementary to the first engagement structure for releasably engaging with the first engagement structure, such that a heart valve attached to the holder is disposed within the rinse cage when the engagement structures are engaged, the rinse cage providing structural protection to the heart valve disposed within during a rinsing operation.

2. A carrier as claimed in claim 1 wherein the holder includes sewing apparatus to which a valve is attachable.

3. A carrier as claimed in claim 1 wherein the holder includes a socket for engaging with a surgical handle.

4. A carrier as claimed in claim 1 wherein the first engagement structure is configured such that the second engagement structure engages with the first engagement structure upon relative linear motion between the holder and the rinse cage.

5. A carrier as claimed in claim 1 wherein the rinse cage has a top member, a side member, and a bottom member;
   at least one of the members having an opening for the passage of fluids.

6. A carrier as claimed in claim 5 wherein the side member is substantially semi-cylindrical.

7. A carrier as claimed in claim 5 wherein the each of the members has at least one opening for the passage of fluid.

8. A carrier as claimed in claim 5 wherein the first engagement structure is disposed on the top member of the rinse cage.

9. A carrier as claimed in claim 8 wherein the first engagement structure includes a channel formed in the top member and extending from an outer edge of the top member to an inner portion of the top member.

10. A carrier as claimed in claim 9 wherein opposed sides of the channel define rails, and the holder has a groove sized to receive the rails;
    a second engagement structure being disposed on the top portion of the holder.

11. A carrier as claimed in claim 10 wherein the holder has a top portion and a bottom portion, with the groove therebetween, and the holder includes sewing apparatus to which a heart valve is attachable.

12. A carrier as claimed in claim 11 wherein the sewing apparatus is disposed on the bottom portion of the holder such that the sewing apparatus is below the top member of the rinse cage when the engagement structures are engaged.

13. A carrier as claimed in claim 10 wherein the channel has a width that decreases from the outer edge to the inner portion.

14. A carrier as claimed in claim 13 wherein the first engagement structure includes a seat disposed at an inner portion of the top member of the rinse cage, the seat being continuous with the channel such that the groove is received in the seat when slid through the channel.

15. A carrier as claimed in claim 14 wherein the width of the channel inner portion is less than a width of the groove, the channel thus defining a neck at the inner portion such that the groove must be urged into and out of the seat.

16. A carrier as claimed in claim 15 wherein the second engagement structure includes a stop configured to limit rotation of the holder relative to the rinse cage.

17. A carrier as claimed in claim 16 wherein the stop projects into the channel when the groove is received in the seat.

18. A carrier as claimed in claim 1, the carrier further comprising a jar, wherein the rinse cage is receivable within the jar.

19. A carrier as claimed in claim 18 further comprising locking structure for limiting rotation of the rinse cage when received in the jar.

20. A carrier as claimed in claim 19 wherein the locking structure includes a receptacle disposed on the rinse cage and a protrusion disposed on the jar, the protrusion being receivable within the receptacle.

21. A carrier as claimed in claim 20 wherein the protrusion is disposed on a bottom of the jar and the receptacle is disposed on the bottom member of the rinse cage.

22. A carrier as claimed in claim 20 wherein the locking structure includes a plurality of the receptacles and a plurality of the protrusions.

23. A carrier as claimed in claim 18 further comprising a lid attachable to the jar and a gasket closely received in the lid.

24. A carrier as claimed in claim 23 wherein the lid includes a flange for retaining the gasket against an inner surface of the lid.

25. A carrier as claimed in claim 24 wherein the flange includes a vent.

26. A carrier as claimed in claim 23 wherein the jar has a rim defining in cross-section an apex for contacting the gasket to form a seal.

27. A carrier-and-heart valve combination, the combination comprising:
- a jar having a lid;
- a rinse cage receivable within the jar, the rinse cage including a first engagement structure disposed thereon;
- a holder including sewing apparatus and a second engagement structure complementary to the first engagement structure for releasably engaging with the first engagement structure;
- a heart valve attached to the sewing apparatus of the holder; and
- preserving fluid received within the jar;
- the engagement structure being configured such that the heart valve is suspended within the rinse cage in the preserving fluid when the engagement structure are engaged.

28. A method for removing a heart valve from a carrier, the method comprising:
- providing a surgical handle with threading;
- providing a carrier with a heart valve including:
- ajar having a lid;
- a rinse cage receivable within the jar, the rinse cage including a first engagement structure disposed on the frame;
- a holder including a socket with threading complementary to that of the surgical handle, sewing apparatus; a second engagement structure complementary to the first engagement structure for releasably engaging with the first engagement structure, and a stop for preventing rotation of the holder relative to the rinse cage;
- locking apparatus disposed on the rinse cage and the jar for preventing rotation of the rinse cage relative to the jar;
- a heart valve attached to the sewing apparatus of the holder; and
- preserving fluid received within the jar; and
- engaging the surgical handle with the socket.

29. A method as claimed in claim 28 wherein the engaging step comprises the step of:
- rotating the surgical handle until the stop limits rotation of the holder and until the locking apparatus limits rotation of the rinse cage.

* * * * *